United States Patent [19]

Bruenemann et al.

[11] 4,053,488
[45] Oct. 11, 1977

[54] SEPARATION OF 1,5-DINITROANTHRAQUINONE AND 1,8-DINITROANTHRAQUINONE

[75] Inventors: Hilmar Bruenemann, Ludwigshafen; Heinz Eilingsfeld, Frankenthal; Dietrich Lach, Ludwigshafen, all of Germany

[73] Assignee: BASF Aktiengesellschaft, Ludwigshafen, Germany

[21] Appl. No.: 723,915

[22] Filed: Sept. 16, 1976

[30] Foreign Application Priority Data

Oct. 11, 1975 Germany .............................. 2545699

[51] Int. Cl.$^2$ .......................... C07C 76/00; C09B 1/00
[52] U.S. Cl. ...................................... 260/369; 260/705
[58] Field of Search ................................. 260/369, 705

[56] References Cited

U.S. PATENT DOCUMENTS 3,929,841  12/1975  Ackermann et al. ................ 260/369

FOREIGN PATENT DOCUMENTS 341,784   6/1972   U.S.S.R.

OTHER PUBLICATIONS

Bikkulov, A. et al., "Recovery of Aromatic Hydrocarbons" in Chem. Ab. 3919c, vol. 78, 1973 p. 327, Abstract of (A).

Primary Examiner—Allen B. Curtis
Attorney, Agent, or Firm—Keil, Thompson & Shurtleff

[57] ABSTRACT

A process for separating 1,5-dinitroanthraquinone and 1,8-dinitroanthraquinone by heating a dinitroanthraquinone mixture, in a mixture of from 5 to 85 per cent by weight of N-methylpyrrolidone and from 95 to 15 per cent by weight of an organic liquid which boils at from 80° to 210° C and is miscible in all proportions with N-methylpyrrolidone, at from 60° to 180° C, and separating off the undissolved material, at the extraction temperature, after the solution equilibrium has been reached. The insoluble material contains more than 85 per cent by weight, and as a rule more than 90 per cent by weight, of 1,5-dinitroanthraquinone. From the extract, it is possible to isolate the dissolved 1,8-dinitroanthraquinone together with the dissolved 1,5-dinitroanthraquinone and any byproducts which may be present.

9 Claims, No Drawings

SEPARATION OF 1,5-DINITROANTHRAQUINONE AND 1,8-DINITROANTHRAQUINONE

The present invention relates to a process for separating 1,5-dinitroanthraquinone and 1,8-dinitroanthraquinone.

U.S. Pat. Application Ser. No. 485,213, now U.S. Pat. No. 3,929,841, discloses a method of isolation of 1,5-dinitroanthraquinone from dinitroanthraquinone mixtures, in which the said mixture is treated with such a quantity of N-methylpyrrolidone, with or without heating, that from 10 to 45 per cent by weight of the mixture remain undissolved. However, this process suffers from the following disadvantages (a) a large amount of N-methylpyrrolidone is required and (b) the parts of the dinitroanthraquinone mixture which are dissolved in the mother liquor are isolated as a residue from the recovery of the extractant, by distilling off the n-methylpyrrolidone used as the said extractant. Because of the high temperatures which occur during the distillation, the products obtained as the residue contain a high proportion of decomposition products. For this reason it is necessary to precipitate the dissolved constituents with water after a part of the extractant has been removed (ie. to precipitate them from the mother liquor when the latter has been concentrated). In doing so, a substantial part of the N-methylpyrrolidone is lost with the water.

It is an object of the present invention to provide a process for separating 1,5-dinitroanthraquinone and 1,8-dinitroanthraquinone in which the extracted constituents can be isolated without substantial losses of extractant and in a very pure form, ie. without significant amounts of decomposition products.

We have found that this object is achieved and that 1,5-dinitroanthraquinone and 1,8-dinitroanthraquinone can be separated by hot extraction of dinitroanthraquinone mixtures, and can be isolated, if the extraction liquid used is a mixture of (a) N-methylpyrrolidone and (b) one or more other organic liquids which have boiling points of from 80° to about 210° C and which are miscible in all proportions with N-methylpyrrolidone, and if the mixture contains from 5 to 85 per cent by weight — based on the weight of the mixture — of N-methylpyrrolidone, and the undissolved material is separated off at the extraction temperature.

Using the process of the invention, the undissolved material obtained is a 1,5-dinitroanthraquinone which as a rule contains from 85 to 97 per cent by weight of the 1,5-dinitro compound. After distilling the organic liquids from the extract, the residue obtained is 1,8-dinitroanthraquinone which still contains, in accordance with their solubility, 1,5-dinitroanthraquinone and the other dinitro compounds present in the dinitroanthraquinone mixture.

It was surprising that the selective dissolving capacity of N-methylpyrrolidone for 1,8-dinitroanthraquinone and for the other $\alpha,\beta'$- and $\beta,\beta'$-dinitroanthraquinones is only affected insignificantly, if at all, by the presence of the organic liquids, even though these liquids are moderate to poor solvents — compared to N-methylpyrrolidone — for 1,8-dinitroanthraquinone.

Examples of such organic liquids (b) are aromatic benzenehydrocarbons, aromatic chlorohydrocarbons, aromatic-aliphatic ethers, aromatic-aliphatic ketones, monohydric alcohols of 3 to 10 carbon atoms, alkanediols of 2 or 3 carbon atoms and aliphatic carboxylic acids of 2 to 6 carbon atoms, the boiling point of these liquids being from 80° to 210° C and preferably from 100° to 170° C, and it being essential that the liquids are miscible in all proportions with N-methylpyrrolidone. Preferably, only one additional organic liquid from the above groups is used with the N-methylprrolidone.

Examples of suitable organic liquids (b) from the above groups are benzene, toluene, ethylbenzene, isopropylbenzene, isobutylbenzene, tert.-butylbenzene, xylene, diisopropylbenzene, diethylbenzene, trimethylbenzene, tetrahydronaphthalene, chlorobenzene, o-dichlorobenzene, chlorotoluene and chloroxylene, anisole and phenetole, acetophenone and propiophenone, n-propanol, n-butanol, isobutanol, hexanol, pentanol, octanol, 2-ethylhexanol, decanol, ethylene glycol, 1,2-propylene glycol, 1,3-propylene glycol, ethylene glycol monomethyl ether, ethylene glycol monoethyl ether, ethylene glycol dimethyl ether, ethylene glycol diethyl ether, acetic acid, propionic acid, butyric acid, isobutyric acid and mixtures of these solvents.

For economic and technical reasons, preferred extraction media are above all those wherein the organic liquid present in addition to N-methylpyrrolidone is ethylene glycol, toluene, ethylbenzene, isopropylbenzene, xylene, tetrahydronaphthalene, chlorobenzene, o-dichlorobenzene, phenetole, anisole, propiophenone or acetophenone. Amongst these, xylene is particularly preferred, for technical reasons.

The extraction medium contains from 5 to 85 per cent by weight, preferably from 20 to 80 per cent by weight, of N-methylpyrrolidone and from 95 to 15 per cent by weight, preferably from 80 to 20 percent by weight, of the additional organic liquid(s).

A particularly good purification effect is achieved with mixtures which contain from 40 to 80 per cent by weight of N-methylpyrrolidone and from 60 to 20 per cent by weight of (b). Since the extracted dinitro compounds can at the same time be isolated under particularly gentle conditions from these mixtures, the mixtures of this composition are particularly preferred extraction media. For the reasons mentioned, a mixture of from 40 to 80 per cent by weight of N-methyl-pyrrolidone and from 60 to 20 per cent by weight of xylene is preferred most of all.

The process according to the invention is advantageously carried out by suspending the mixture of 1,5-dinitroanthraquinone and 1,8-dinitroanthraqinone in the extraction liquid and bringing it into intimate contact with the latter. The extraction, also referred to as treatment in the text which follows, is as a rule carried out at from 60° to 180° C, preferably at from 100° to 160° C. The suspension is kept at the desired temperature or the temperature found to be the optimum for the extraction medium used, until the solution equilibrium has been reached. In general, this is the case after from 0.5 to 6 hours. The undissolved material is then separated from the extraction liquid at the temperature at which the extraction has been carried out. The undissolved material, which contains more than 85 per cent by weight, and as a rule more than 90 per cent by weight, of 1,5-dinitroanthraquinone, is washed with a small amount of pure warm extraction liquid and the latter is then removed by washing with low-boiling solvents, eg. methanol and/or acetone.

The amount of extraction liquid can be varied within wide limits. In order to achieve high yields of pure 1,5-dinitroanthraquinone, the amount is so chosed that all the 1,8-dinitro compound, and any $\alpha,\beta'$ and $\beta,\beta'$- dinitro compounds which may be present, are dissolved. As a rule the amount used is from 1 to 20 times, preferably from 3 to 10 times, the amount by weight of the dinitroanthraquinone mixture. As the content of N-methylpyrrolidone increases, the amounts of extraction liquid required become smaller, and vice versa they become larger as the content of N-methylpyrrolidone decreases.

The amount of extraction liquid required also depends on the temperature at which the extraction is carried out. At a given composition, a smaller amount of extraction liquid is required at a higher temperature than at a lower temperature.

The amount of extraction liquid required for the separation furthermore depends on the composition of the dinitroanthraquinone mixture which is to be separated. A higher contend of 1,5-dinitroanthraquinone requires smaller amounts of extraction liquid, and vice versa.

After the extraction, the extracton liquid above all contains 1,8-dinitroanthraquinone, but in addition also — in accordance with their solubility — some 1,5-dinitroanthraquinone and the $\alpha,\beta'$- and $\beta,\beta'$-dinitroanthraquinones which may have been present in the dinitroanthraquinone mixture, eg. 1,6-, 1,7-, 2,6- and 2,7-dinitroanthraquinone.

A part of the 1,8-dinitro compound can be precipitated from the extract (mother liquor) by cooling. The dinitro compounds dissolved in the liquid can also be precipitated by adding suitable organic diluents or even by adding water. However, the extract is preferaby worked up by distillation under reduced pressure, in which case the dissolved dinitroanthraquinones are obtained as a solid residue. Since the heat exposure of the material is slight, due to the presence of the additional solvent, the extracted compounds obtained as the residue are in a comparatively pure form.

It is a disadvantage that in addition to 1,8-dinitroanthraquinone the extract still contains substantial amounts of the $\alpha,\beta'$- and $\beta,\beta'$-dinitroanthraquinones. U.S. Pat. Application Ser. No. 686,365 has proposed treating (extracting) dinitroanthraquinone mixtures, which are obtained by dinitration of anthraquinone and which in addition to 1,5-dinitroanthraquinone and 1,8-dinitroanthraquinone still contain about 20 per cent be weight of $\alpha,\beta'$- and $\beta,\beta'$-dinitroanthraquinones, with hot xylene, which essentially dissolves the $\alpha,\beta'$- and $\beta,\beta'$-dinitroanthraquinones. The residue obtained is a mixture of 1,5-dinitroanthraquinone and 1,8-dinitroanthraquinone, which contains more than 90 per cent by weight, and preferably more than 95 per cent by weight, of 1,5-dinitroanthraquinone and 1,8-dinitroanthraquinone. If such pre-purified dinitroanthraquinone mixtures are used as the starting material for the process according to the invention, pure 1,5-dinitroanthraquinone is obtained and in addition the extract gives a 1,8-dinitro anthraquinone which contains from 70 to 80 percent by weight of the 1,8-dinitro compound.

If the purification is carried out according to U.S. pat. application Ser. No. 686,365, the mixture of 1,5-dinitroanthraquinone and 1,8-dinitroanthraquinone is obtained as a filter residue containing xylene. This material, moist with xylene, can then be separated directly, by the process according to the invention, into 1,5-dinitroanthraquinone and 1,8-dinitroanthraquinone, using a mixture of N-methylpyrrolidone and xylene, without first having to dry the starting material.

The combination of the process of the invention with the process proposed in U.S. pat. application Ser. No. 686,365 permits economical purification and separation of the 1,5-dinitroanthraquinone and 1,8-dinitroanthraquinone present in the dinitroanthraquinone mixtures.

The Examples which follow illustrate the process according to the invention. Parts and percentages mentioned below are by weight. The composition of the products was determined by gas chromatography. NMP = N-methylpyrrolidone.

EXAMPLE 1

160 parts of a dinitroanthraquinone mixture which contains 55% of 1,5-dinitroanthraquinone, 42% of 1,8-dinitroanthraquinone, 2% of 1,6- and 1,7-isomers and 1% of 1-nitroanthraquinone are suspended in 174 parts of xylene and 612 parts of N-methylpyrrolidone (NMP). The mixture is stirred for 3 hours at 70° C, the suspension is then filtered at 70° C and the residue is washed with 100 parts of xylene. After drying, 81.2 parts of a residue which contains 92% of 1,5-dinitroanthraquinone are obtained. The mother liquor is concentrated to dryness under reduced pressure. 78.6 parts of residue containing 77% of 1,8-dinitroanthraquinone are obtained.

EXAMPLE 2

50 parts of the dinitroanthraquinone mixture from Example 1 are stirred for 2 hours in a mixture of 204 parts of NMP and 55 parts of chlorobenzene at 80° C. The product is then filtered off at 80° C and washed with 50 parts of chlorobenzene. The further working up is carried out as described in Example 1. 24.3 parts of 1,5-dinitroanthraquinone (94% pure) and 25.6 parts of 1,8-dinitroanthraquinone (75% pure) are obtained.

EXAMPLES 3 to 6

The procedure described in Example 2 is followed, but instead of chlorobenzene the solvents shown in the Table are used.

| | | Yield | | | |
|---|---|---|---|---|---|
| | | 1,5-dinitroanthraquinone | | 1,8-dinitroanthraquinone | |
| Ex. | Parts of solvent | Parts | Purity [%] | Parts | Purity [%] |
| 3 | 50 ethylbenzene | 25.1 | 92 | 24.8 | 76 |
| 4 | 50 toluene | 24.9 | 92 | 24.9 | 76 |
| 5 | 46 ethylene glycol monomethyl ether | 24.6 | 92 | 25.3 | 76 |
| 6 | 50 acetic acid | 25.3 | 91 | 24.6 | 76 |

EXAMPLE 7

160 parts of the mixture of 1,5-dinitroanthraquinone and 1,8-dinitroanthraquinone referred to in Example 1, 230 parts of xylene and 540 parts of NMP are stirred for 3 hours at 80° C. The mixture is then worked up as described in Example 1. 81.6 parts of 1.5-isomer (92% pure) and 78.1 parts of 1,8-isomer (77% pure) are obtained.

EXAMPLE 8

160 parts of a mixture of 1,5-dinitroanthraquinone and 1,8-dinitroanthraquinone of the composition described in Example 1 are stirred for 2 hours in 318 parts of xylene and 440 parts of NMP at 100° C. The mixture is then worked up as described in Example 1. The yield is 79.4 parts of 1,5-dinitroanthraquinone (93% pure) and 81.1 parts of 1,8-dinitroanthraquinone (76% pure).

EXAMPLE 9

The procedure followed is as described in Example 8, except that the dinitroanthraquinone mixture is stirred for 1 hour in 444 parts of xylene and 300 parts of NMP at 130° C. 82.5 parts of 1,5-dinitroanthraquinone (91% pure) and 77.3 parts of 1,8-dinitroanthraquinone (77% pure) are obtained.

EXAMPLE 10

50 parts of the mixture of 1,5-dinitroanthraquinone and 1,8-dinitroanthraquinone referred to in Example 1 are stirred for 2 hours in 360 parts of anisole and 37 parts of NMP at 140° C. The mixture is worked up as indicated in Example 1.

Yield: 24.7 parts of 1,5-dinitroanthraquinone (93% pure) and 25.2 parts of 1,8-dinitroanthraquinone (76% pure).

EXAMPLE 11

The procedure followed is as described in Example 10, except that a mixture of 390 parts of acetophenone and 31 parts of NMP is used as the solvent. Yield: 24.3 parts of 1,5-dinitroanthraquinone (94% pure) and 25.7 parts of the 1,8-isomer (76% pure).

EXAMPLE 12

The procedure followed is as described in Example 10, except that a mixture of 548 parts of tetralin and 64 parts of NMP is used as the solvent. Yield: 25.0 parts of 1,5-isomer (92% pure) and 24.9 parts of 1,8-isomer (76% pure).

EXAMPLE 13

50 parts of the mixture of 1,5-dinitroanthraquinone and 1,8-dinitroanthraquinone described in Example 1 are stirred for 2 hours in 360 parts of phenetole and 37 parts of NMP at 140° C. The mixture is worked up as described in Example 1. The yield is 23.4 parts of 1,5-dinitroanthraquinone (95% pure) and 26.2 parts of 1,8-dinitroanthraquinone (76% pure).

EXAMPLE 14

The procedure followed is as described in Example 10, with 390 parts of propiophenone and 31 parts of NMP as the solvent. Yield: 19.5 parts of 1,5-dinitroanthraquinone (97% pure) and 30.4 parts of 1,8-dinitroanthraquinone (67% pure).

EXAMPLE 15

The procedure followed is as described in Example 10, with 600 parts of tetralin and 80 parts of NMP as the solvent. Yield: 23 parts of 1,5-dinitroanthraquinone (95% pure) and 26.9 parts of 1,8-dinitroanthraquinone (75% pure).

EXAMPLE 16

The procedure followed is as described in Example 10, with 588 parts of o-dichlorobenzene and 51 parts of NMP as the solvent. Yield: 24.3 parts of 1,5-dinitroanthraquinone (93% pure) and 25.7 parts of 1,8-dinitroanthraquinone (76% pure).

EXAMPLE 17

100 parts of a mixture of 1,5-dinitroanthraquinone and 1,8-dinitroanthraquinone, which contains 10% of 1,5-isomer, are stirred for 3 hours in 510 parts of NMP and 435 parts of xylene at 120° C. The mixture is then worked up as described in Example 1. Yield: 7 parts of 1,5-dinitroanthraquinone (90% pure) and 93 parts of 1,8-dinitroanthraquinone (96% pure).

EXAMPLE 18

100 parts of a mixture of 1,5-dinitroanthraquinone and 1,8-dinitroanthraquinone, which contains 90% of 1,5-isomer, are stirred for 3 hours in 105 parts of NMP and 85 parts of xylene at 60° C. The mixture is then worked up as described in Example 1. Yield: 90.3 parts of 1,5-dinitroanthraquinone (99.5% pure) and 9.7 parts of 1,8-isomer (98.1% pure).

EXAMPLE 19

160 parts of a mixture of 1,5-dinitroanthraquinone and 1,8-dinitroanthraquinone from Example 1 are stirred for 3 hours at 80° C in 775 parts of a mixture of NMP and xylene, which contains 28% of xylene. After working up as described in Example 1, 79.4 parts of 1,5-dinitroanthraquinone (93% pure) and 80.4 parts of 1,8-dinitroanthraquinone (77% pure) are obtained.

EXAMPLE 20 and 21

The procedure followed is as in Example 19, but a mixture which has the xylene content shown in the Table below is used.

| | | | Yield | | | |
|---|---|---|---|---|---|---|
| | | | 1,5-Dinitroanthraquinone | | 1,8-Dinitroanthraquinone | |
| Ex. | Temp. | % Xylene | (Parts) | Purity (%) | (Parts) | Purity (%) |
| 20 | 90° C | 34.2 | 79.0 | 93 | 80.8 | 76 |
| 21 | 100° C | 41.3 | 79.3 | 93 | 80.7 | 77 |

EXAMPLE 22

267 parts of a mixture of 1,5-dinitroanthraquinone and 1,8-dinitroanthraquinone, which contains 40% of xylene, are stirred in 306 parts of NMP and 435 parts of xylene. To begin with, 107 parts of xylene are distilled off at 170° C. The mixture is then cooled to 140° C, stirred at this temperature for one hour and then worked up as described in Example 1. Yield: 79.6 parts of 1,5-dinitroanthraquinone (93% pure) and 79.7 parts of 1,8-dinitroanthraquinone (77% pure).

EXAMPLE 23

160 parts of a dinitroanthraquinone mixture which contains 47% of 1,5-dinitroanthraquinone, 41% of 1,8-dinitroanthraquinone, 6% of 1,6-dinitroanthraquinone, 5% of 1,7-dinitroanthraquinone and 1% of 1-nitroanthraquinone is stirred for three hours in 306 parts of NMP and 435 parts of xylene at 130° C. It is then worked up as described in Example 1. Yield: 65.6 parts of 1,5-dinitroanthraquinone (97% pure) and 84.5 parts of 1,8-dinitroanthraquinone (70% pure).

We claim:

1. A process for separating 1,5-dinitroanthraquinone and 1,8-dinitroanthraquinone which comprises heating a dinitroanthraquinone mixture, in a mixture of (a) from 5 to 85 percent by weight of N-methylpyrrolidone and (b) from 95 to 15 percent by weight of at least one aromatic benzenehydrocarbon, aromatic chlorohydrocarbon, aromatic-aliphatic ether, aromatic-aliphatic ketone, monohydric aliphatic alcohol of 3 to 10 carbon atoms, alkanediol of 2 or 3 carbon atoms, aliphatic carboxylic acid of 2 to 6 carbon atoms or mixtures thereof, the boiling points of the respective constituents of (b) being from 80° to about 210° C and said constituents (b) being miscible in all proportions with N-methylpyrrolidone, at from 60° to 180° C and when the solution equilibrium has been reached, separating the undissolved material from the liquid phase at the extraction temperature.

2. A process as claimed in claim 1, wherein the mixture contains, as (b), toluene, ethylbenzene, xylene, tetrahydronaphthalene, chlorobenzene o-dichlorobenzene, anisole, phenetole, acetophenone, propiophenone, ethylene glycol or a mixture of these components.

3. A process as claimed in claim 1, wherein the mixture comprises from 20 to 80 percent by weight of (a) and from 80 to 20 percent by weight of (b).

4. A process as claimed in claim 2, wherein the mixture comprises from 20 to 80 percent by weight of (a) and from 80 to 20 percent by weight of (b).

5. A process as claimed in claim 2, wherein the mixture comprises from 40 to 80 percent by weight of (a) and from 60 to 20 percent by weight of (b).

6. A process as claimed in claim 1, wherein the mixture contains from 40 to 80 percent by weight of N-methylpyrrolidone and from 60 to 20 percent by weight of xylene.

7. A process as claimed in claim 2, wherein the dinitroanthraquinone mixture, in the mixture of (a) and (b), is heated at from 100° to 160° C.

8. A process as claimed in claim 6, wherein the dinitroanthraquinone mixture, in the mixture of (a) and (b), is heated at from 100° to 160° C.

9. A process as claimed in claim 4, wherein the dinitroanthraquinone mixture, in the mixture of (a) and (b), is heated at from 100° to 160° C.

* * * * *